United States Patent [19]

Ebata et al.

[11] Patent Number: 5,216,177

[45] Date of Patent: Jun. 1, 1993

[54] METHOD OF PREPARING TRANS-3,4-DISUBSTITUTED-γ-LACTONES

[75] Inventors: Takashi Ebata; Hajime Matsushita; Hiroshi Kawakami; Koshi Koseki, all of Kanagawa, Japan

[73] Assignee: Japan Tobacco Inc., Tokyo, Japan

[21] Appl. No.: 695,010

[22] Filed: May 3, 1991

[30] Foreign Application Priority Data

May 8, 1990 [JP] Japan ................................. 2-116766
Nov. 30, 1990 [JP] Japan ................................. 2-338645

[51] Int. Cl.$^5$ ........................................... C07D 307/33
[52] U.S. Cl. ..................................................... 549/295
[58] Field of Search ........................................ 549/295

[56] References Cited

U.S. PATENT DOCUMENTS 3,926,947 12/1975 Lipska .................................. 536/1.1

FOREIGN PATENT DOCUMENTS 0411403 2/1991 European Pat. Off. .

OTHER PUBLICATIONS

March, J. *Advanced Org. Chem.*, pp. 400–401.
March, *Advanced Organic Chemistry*, Third Edition, pp. 310–317 (John Wiley & Sons, New York).
*McGraw-Hill Dictionary of Scientific and Technical Terms*, Fourth Edition, pp. 187 and 1392 (McGraw-Hill Book Co., New York).
Ortuno et al., Tetrahedron, vol. 43, No. 19, pp. 4497–4506 (1987).
Hoppe et al., Angew. Chem. Int. Ed. Engl., vol. 28, No. 1, pp. 69–71 (1989).
Shibagaki et al.; Chemistry Letters, pp. 307–310 (1990).
Mori et al., Carbohydrate Research, vol. 129, pp. 73–86 (1984).
Marshall et al., J. Org. Chem., vol. 49, pp. 747–753 (1984).
Ebata et al., Heterocycles, vol. 31, No. 9, pp. 1585–1588 (1990).

*Primary Examiner*—C. Warren Ivy
*Assistant Examiner*—A. A. Owens
*Attorney, Agent, or Firm*—Birch, Stewart, Kolasch & Birch

[57] ABSTRACT

First, levoglucosenone is made to react with methyl lithium in the presence of copper iodide in order to introduce a methyl group into an enone group of levoglucosenone, and to obtain 1,6-anhydro-3,4-dideoxy-4-C-methyl-β-D-erythro-hexopyranose-2-ulose. This methyl compound is oxidized in acetic acid for lactone formation, and (3S,4S)-5-hydroxy-3-methylpentan-4-olide is thus obtained. Further, this lactone is made to react with tosyl chloride in anhydrous pyridine to obtain (3S,4S)-3-methyl-5-tosyloxypentan-4-olide (tosylate). The obtained tosylate is alkylated with n-propyl lithium in the presence of copper iodide to obtain (3S,4R)-3-methyl-4-octanolide. Here, the (3S,4S)-3-methyl-5-tosyloxypentan-4-olide may be treated with potassium carbonate to cleave lactone ring once, thereby obtaining epoxide. After that, the obtained epoxide is alkylated to form lactone ring again to obtain (3S,4R)-3-methyl-4-octanolide.

41 Claims, No Drawings

METHOD OF PREPARING TRANS-3,4-DISUBSTITUTED-γ-LACTONES

BACKGROUND OF THE INVENTION

1. Field of the Invention

This invention relates to a method of preparing trans-3,4-disubstituted-γ-lactones. The lactones are contained, for example, in fragrance ingredients and insect pheromones.

2. Description of the Related Art

Many trans-3,4-disubstituted-γ-lactones having substituents such as an alkyl group or an alkenyl group at the 3 and 4 positions such that they are in positions trans to each other, are present in the natural world. For example, they are important fragrance ingredients contained in whisky, cognac, etc. They are also utilized as pheromones in the insect world.

Trans-3,4-disubstituted-γ-lactones are generally present in the optically active form. Different features such as biological activity, etc., are often recognized between two optical isomers of the lactones. Therefore, it is extremely important to develop a method for synthesizing optical isomers of trans-3,4-disubstituted-γ-lactones in chemically pure form.

One of the trans-3,4-disubstituted-γ-lactones as described above is lactone (I) of the following general formula (I):

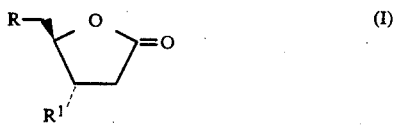

wherein R and $R^1$ are general alkyl or alkenyl groups.

Conventionally, various methods have been developed to prepare the lactone (I). Examples of the conventional methods include the following:

1) A method utilizing ribonolactone as a starting material (*Tetrahedron*, Vol. 43, 4497–4506 (1987)).
2) A method utilizing asymmetric synthesis (*Agnew. Chem. Int. Ed. Engl.*, Vol. 28, 69–71 (1989)).

However, method 1) is not practical, because, ribonolactone which is the starting material is expensive, and the reaction steps in method 1) are complicated.

Method 2) has the following disadvantages: one is that it is necessary to use a specific reagent such as (−)-sparteine, and another is that the optical purity of products obtained via method 2) is not sufficiently high.

SUMMARY OF THE INVENTION

An object of the invention is to produce a method of preparing trans 3,4-disubstituted-γ-lactones, via which optically active lactones of high purity can be easily obtained.

This object is attained by utilizing levoglucosenone which is known as a pyrolytic product of cellulose as a starting material and forming lactone rings according to Baeyer Villiger oxidation.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

DETAILED DESCRIPTION OF THE PREFERRED EMBODIMENTS

The inventors of the present invention have extensively studies in order to overcome the disadvantages described above, and completed the invention by finding that trans-3,4-disubstituted-γ-lactones (I) of high optical purity can be easily obtained by utilizing levoglucosenone as a starting material and forming lactone rings according to Baeyer Villiger oxidation. Specifically, this invention provides a method for preparing trans-3,4-disubstituted-γ-lactones, comprising steps of:

(a) adding alkyl or alkenyl group $R^1$ to an enone group in levoglucosenone shown in the following general formula (VI), thereby obtaining a compound (V) of the following general formula (V),

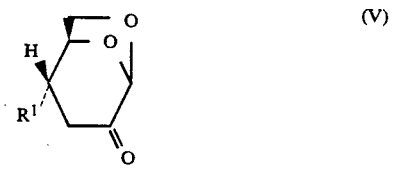

wherein $R^1$ is a general alkyl or alkenyl group, (b) oxidizing the obtained compound (V) with a peracid, thereby obtaining a compound (IV) of the following general formula (IV),

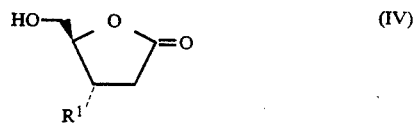

wherein $R^1$ is the same as above, (c) converting the hydroxyl group of the obtained compound (IV) into leaving group $OR^2$, thereby obtaining a compound (III) of the following general formula (III),

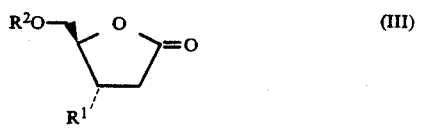

wherein $R^1$ is the same as above, and $OR^2$ is a general leaving group, and (d) alkylating or alkenylating the obtained compound (III), thereby obtaining said compound (I).

Also, according to the present invention to provide a method of preparing trans-3,4-disubstituted-γ-lactones, the compounds obtained in the step (c) may be treated with a base to cleave the lactone ring once, and subjecting the obtained compound (II) of the following general formula (II) obtained to alkylation or alkenylation in step (d), thereby obtaining the compound (I),

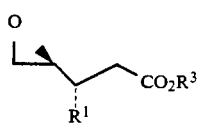

(II)

wherein $R^1$ is the same as above, and $R^3$ is a hydrogen atom or a general alkyl group.

According to the method of the present invention, the optical purity of levoglucosenone used as a starting material can be maintained as it is. Therefore, trans-3,4-disubstituted-γ-lactones (I) of high optical purity can be obtained.

The method according to the present invention is described in detail as follows.

As a starting material of the present invention, levoglucosenone (VI) is utilized, which is known as a pyrolytic product of cellulose. Levoglucosenone (VI) of high optical purity can be obtained utilizing galactose as a starting material according to the method described in *Chemistry Letters* (307–310 pp. (1990)).

An additional reaction in step (a) which introduces an alkyl or alkenyl group to an enone group of levoglucosenone (VI) is performed in the presence of copper salts such as copper iodide, copper bromide, or copper chloride by utilizing alkylating agents such as alkyl lithium, alkyl magnesium, etc., or alkenylating agents such as alkenyl lithium, alkenyl magnesium, etc. In this case, the amount of the alkylating agent or the alkenylating agent with respect to one mole of levoglucosenone is preferably 1.0 to 3.0 moles, more preferably 1.0 mole. For example, this reaction is performed in an adequate solvent, under an inert gas atmosphere, generally at $-70°$ C. to room temperature, for 30 minutes to two hours, with stirring. Examples of adequate solvents utilized here are organic solvents such as ethers, for example diethyl ether, tetrahydrofuran, etc., toluene, or xylene, but are not restricted thereto.

When an alkyl or alkenyl group ($R^1$) is introduced in step (a), the desired group can be easily introduced by adequately selecting an alkylating or alkenylating agent. $R^1$ which is introduced is generally preferably an alkyl or alkenyl group having not more than 10 carbons.

The reaction to form a lactone ring in step (b) can be performed according to Baeyer Villiger oxidation utilizing an adequate peracid. In this case, the amount of peracid to one mole of the compound (V) is preferably one to five moles, more preferably one mole. Examples or peracid which can be used in this lactone ring formation include peracids such as peracetic acid, performic acid, methachloro perbenzoic acid, and a peroxide of phthalic acid. Formation of the lactone ring is performed utilizing these peracids in an adequate solvent, at 0° to 5° C., for one to 80 hours, with stirring.

Examples of adequate solvents here include acids such as acetic acid and formic acid, and halogen series solvents such as methylene chloride and chloroform. However, the solvent is not restricted thereto, as long as it does not react with the peracid, and produces no by products which make after-treatments difficult.

The reaction in step (c) to convert the hydroxyl group of the compound (VI) to the leaving group $OR^2$ can be performed by causing the $R^2$ group to combine with the oxygen atom of the hydroxyl group by general esterification. Since the $OR^2$ group is eliminated in step (d) as will be described as follows, this group may be a general leaving group and is not restricted to a specific one. However, preferred a $R^2$ group is, for example, a paratoluene sulfonyl group, a methane sulfonyl group, or a trifluoromethane sulfonyl group. In order to introduce leaving group $OR^2$, for example, compounds having $R^2$ group such as halides of $R^2$ and acid anhydrides of $R^2$ are made to react in an adequate solvent with stirring at $-10°$ to 30° C. for three to thirty hours. In this case, the amount of compound having said $R^2$ group to one mole of the compound (IV) is preferably one to four moles, more preferably 1.3 moles. The solvent here may be pyridine or triethylamine, but is not restricted thereto.

Alkylation and alkenylation in step (d) can be performed, for example, by utilizing alkylating agents such as alkyl lithium, alkyl magnesium, etc., and alkenylating agents such as alkenyl lithium, alkenyl magnesium, etc., in the presence of copper salts such as copper iodide, copper bromide, and copper chloride. This reaction may be performed, for example, in an adequate solvent in an inert gas atmosphere at $-70°$ C. to room temperature for one to twenty hours, with stirring. Solvents used here may be organic solvents such as toluene, xylene, etc., but are not restricted thereto.

Before step (d), the compound (III) obtained in step (c) may be also treated with a base, thereby cleaving the lactone ring of the compound (III) once, and obtaining epoxide (II). Compound (III) can be allowed to react with a base in an adequate solvent at 0° to 30° C. for two to thirty hours with stirring. The base may be a metallic hydroxide such as potassium hydroxide, sodium hydroxide or lithium hydroxide, a carbonate such as potassium carbonate or sodium carbonate, or an acetate such as potassium acetate or sodium acetate. In this case, the amount of the base to one mole of the compound (III) is preferably one to three moles, more preferably 1.1 moles. Examples of the adequate solvent used here include water, alcohols such as methanol and ethanol, and a mixture of these solvents with tetrahydrofuran, etc., but is not restricted thereto.

Further, when an alcohol is used as a solvent here, an alkyl group corresponding thereto is introduced as the $R^3$ group of the compound (II). However, this alkyl group need not be restricted to a specific one, since it is eliminated in step (d).

By subjecting the compound (II) thus obtained to the alkylating or alkenylating in step (d) as described above in the place of the compound (III), the objective compound (I) can be obtained.

EXAMPLES

The present invention will be further described in detail according to the following examples.

EXAMPLE 1

Preparation of Trans-Whisky Lactone Part I

[A] Preparation of 1,6-anhydro-3,4-dideoxy-4-C-methyl-β-D-erythro-hexopyranose-2-ulose To dimethyl copper lithium solution prepared by adding 66.6 g of copper iodide (350 mmol) to 500 ml of methyl lithium (1.4 N, 700 mmol) according to a general method, 50 ml of anhydrous ether solution in which 44.1 g of levoglucosenone (350 mmol) is dissolved were added dropwise at $-60°$ C. Thereafter, the resultant solution was stirred at $-60°$ C. for thirty minutes, and then its reaction temperature was raised to $-20°$ C. Next, the reacted solution was poured into saturated ammonium chloride aqueous solution, followed by stirring at room temperature for an hour, The resultant solution was filtered to remove insoluble substances. Next, the organic solvent layer was separated from the obtained filtrate. The residual aqueous layer was extracted with methylene chloride to obtain an extract, This extract and the organic layer as separated before were combined. The organic layer thus combined was washed with a saturated aqueous sodium chloride solution, and dried with anhydrous magnesium sulfate. The resultant organic layer was further filtered, and the filtrate was concentrated. The obtained residue was distilled under reduced pressure, thereby yielding 41.9 g of 1,6-anhydro-3,4-dideoxy-4-C-methyl-$\beta$-D-erythrohexopyranose-2-ulose (yield: 84.3%). This product exhibited the following physical properties;

m.p.: 122°–125° C./26 mmHg.
$n_D^{23}$ 1.4673.
$[\alpha]_D^{23}$ −2;93° (c=0.36, Et$_2$O).
$^1$H NMR(CDCl$_3$): $\delta$
1.22 (3H, d, J=7.0Hz),
2.0–2.15 (1H, m),
2.25–2.42 (1H, m)
2.83 (1H, dd, J=7.8 and 16.3Hz)
3.98 (1H, dd, J=5.2 and 7.5Hz),
4.03 (1H, dd, J=1.2 and 7.5Hz),
4.40–4.46 (1H, m),
5.06 (1H, s).

[B] Preparation of (3S, 4S)-5-hydroxy-3-methylpentan-4-olide 5 g of 1,6anhydro-3,4-dideoxy-4-C-methyl-$\beta$-D-erythro-hexopyranose-3-ulose (35.2 mmol) obtained in step [A] were dissolved into 37 ml of acetic acid. To the resultant solution, 6.7 ml of 40% peracetic acid were added dropwise with stirring. During this addition, the reaction temperature was maintained at 20°–30° C. Next, the obtained solution was stirred at room temperature overnight, To the reacted solution, 2.4 g of dimethyl sulfide (38.7 mmol) were added dropwise with cooling. The obtained solution was further stirred at room temperature for thirty minutes. The reacted solution was then concentrated, and the obtained residue was dissolved in 30 ml of methanol. To the resultant solution, 10 drops of concentrated hydrochloric acid were added and stirred with heating at 50° C. for six hours. After the obtained solution was concentrated, the resultant residue was purified via silica gel column chromatography (n-hexane:ethyl acetate=1:1 to 1:3) to obtain 3.94 g of (3S,4S)-5-hydroxy-3-methylpentan-4-olide (yield: 86.0%). This product exhibited the following physical properties:

m.p.: 104°–105° C./0.05 mmHg.
$[\alpha]_D^{23}$ +79° (c=1.0, CHCl$_3$).
$^1$H NMR (CDCl$_3$):$\delta$
1.18 (3H, d, J=6.7Hz),
2.23 (1H, dd, J=8.7 and 17.3Hz),
2.45–2.62 (1H,·m),
2.76 (1H, dd, J=8.6 and 17.3Hz),
2.81 (1H, br, s),
3.61–3.74 (1H, m),
3.85–3.96 (1H, m),
4.09–4.19 (1H, m).

[C] Preparation of (3S, 4S)-3-methyl-5-tosyloxypentan-4-olide

In 60 ml of anhydrous pyridine, 7.9 g of (3S, 4S)-5-hydroxy-3-methylpentan-4-olide (60.8 mmol) obtained in step [B] were dissolved. To the resultant solution, 15.1 g of tosyl chloride (79.0 mmol) were added with cooling by ice. The obtained mixture was stirred at room temperature overnight. The reacted solution was poured into a diluted hydrochloric acid solution which had been cooled, and extracted with methylene chloride. The obtained extract was washed with water and a saturated sodium chloride aqueous solution, in this order, and dried with anhydrous magnesium sulfate. Next, the obtained solution was filtered, and the obtained filtrate was concentrated. The obtained residue was purified via silica gel column chromatography (n-hexane:ethyl acetate=5:1 to 1:2) to obtain 14.8 g of (3S,4S)-3-methyl-5-tosyloxypentan-4-olide (tosylate) (yield: 85.5%). This product exhibited the following physical properties:

$^1$H NMR (CDCl$_3$): $\delta$
1.16 (3H, d, J=6.8Hz),
2.19 (1H, dd, J=8.1 and 17.4Hz),
2.35–2.56 (4H, m),
2.72 (1H, dd, J=8.6 and 17.4Hz),
4.10–4.25 (3H, m),
7.39 (2H, d, J=8.5Hz),
7.78 (2H, d, J=8.5Hz).

The obtained tosylate was utilized for the following reaction without additional purification.

[D] Preparation of (3S,4R)-3-methyl-4-octanolide (trans-whisky lactone)

In 20 ml of anhydrous ether, 1.98 g of copper iodide (10.4 mmol) were suspended. To the obtained suspension, 20.8 ml of n-propyl lithium solution (1.0 N, 20.8 mmol) were added dropwise under an argon atmosphere with cooling at −50° C. Next, the resultant suspension was added dropwise into a mixture solution of 10 ml of anhydrous ether in which 1.97 g of tosylate (6.93 mmol) obtained in step [C] were dissolved, and 10 ml of toluene, under an argon atmosphere at −60° C. Next, the temperature of the reacted solution was raised from −60° C. to −20° C. over three hours. After that, the reacted solution was poured into a saturated aqueous ammonium chloride solution, then the obtained solution was stirred for thirty minutes, and filtered to remove insoluble substances. The obtained filtrate was extracted with ether, and the resultant extract was washed with water and a saturated aqueous sodium chloride solution, in this order. The resultant extract was then dried with anhydrous magnesium sulfate, and filtered. The filtrate was then concentrated. The obtained residue was dissolved in 20 ml of methanol, and 20 ml of 10% sodium hydroxide were added, and the solution was stirred at room temperature for three hours. After that, the methanol in the solution was distilled off under reduced pressure, the obtained residue was extracted twice with diethyl ether, and then the organic layer was separated from the obtained extract. Also, the residual aqueous layer was acidified with dilute hydrochloric acid, and extracted with diethyl ether five times. The obtained extract was combined with the organic layer as obtained before. The combined organic layer was dried with anhydrous magnesium sulfate, and concentrated to obtain the crude product. This crude product was purified via silica gel column chromatogrpahy (n-hexane:ether=10:1 to 2.1) and distilled under reduced pressure to obtain 763 mg of (3S,4R)-3-methyl-4-octanolide (trans-whisky lactone) (yield: 70.6%). This product exhibited the following properties:

m.p.: 123°-125° C./16 mmHg.
$n_D^{23}$ 1.4402.
$[\alpha]_D^{23}$ +79.5° (c=1.0, MeOH).
$^1$H NMR(CDCl$_3$): δ
0.92 (3H, t, J=7.2Hz),
1.14 (3H, d, J=6.4Hz),
1.30–1.75 (6H, m),
2.12–2.31 (2H, m),
2.60–2.75 (1H, m),
3.97–4.05 (1H, m).

EXAMPLE 2

Preparation of Trans-Whisky Lactone Part II

[C'] Preparation of (3S, 4S)-4,5-epoxy-3-methylpentanoate

To 60 ml of methanol, 14.8 g of the tosylate (52.1 mmol) obtained in step [C] in Example 1 were dissolved. To the resultant solution, 7.91 g (57.3 mmol) of potassium carbonate were added with stirring and cooling by ice. The obtained solution was stirred at room temperature overnight; 100 ml of n-hexane and 50 ml of diethylether were added. The obtained solution was filtered to remove insoluble substances. The resultant filtrate was concentrated at atmospheric pressure. The obtained residue was distilled under reduced pressure to obtain 5.83 g of (3S,4S)-4,5-epoxy-3-methylpentanoate (epoxide) (yield: 77.7%). This product exhibited the following physical properties:
m.p.: 93°-95° C./26 mmHg.
$n_D^{23}$ 1.4278.
$[\alpha]_D^{23}$ −1.73° (c=1.22, dioxan).
$^1$H NMR(CDCl$_3$): δ
1.05 (3H, d, J=6.9Hz),
1.59–1.95 (1H, m),
2.29 (1H, dd, J=8.3 and 15.2Hz),
2.50–2.60 (2H, m),
2.75–2.84 (2H, m),
3.70 (3H, s).

[D'] Preparation of (3S, 4R)-3-methyl-4-octanolide (trans-whisky lactone)

In 20 ml of anhydrous ether, 1.98 g of copper iodide (10.4 mmol were suspended. To the resultant suspension, 20.8 ml of n-propyl lithium solution (1 N, 20.8 mmol) were added dropwise under an argon atmosphere with cooling at −50° C. The reacted solution was added dropwise to 25 ml of anhydrous ether solution containing 1.0 g of epoxide (6.94 mmol) obtained in step [C'] under an argon atmosphere at −60° C. Next, the temperature of the reacted solution was raised from −60° C. to −20° C. over three hours. After that, the solution was poured into a saturated aqueous ammonium chloride solution, followed by stirring for thirty minutes. Next, the solution was filtered to remove insoluble substances. The obtained filtrate was extracted with ether. The resultant extract was then washed with water and a saturated aqueous sodium chloride aqueous solution, in this order, dried with anhydrous magnesium sulfate, and filtered. The obtained filtrate was concentrated, and the obtained residue was dissolved in 20 ml of methanol. To the obtained solution was then added 20 ml of a 10% aqueous sodium hydroxide solution, followed by stirring at room temperature for three hours. Next, the methanol in the solution as distilled off under reduced pressure, and the obtained residue was extracted twice with diethyl ether and then the organic layer was separated from the obtained extract. Also, the residual aqueous layer was acidified with dilute hydrochloric acid, and then extracted five times with diethyl ether. The obtained extract was combined with the organic layer obtained before. The combined organic layer was dried with anhydrous magnesium chloride, and concentrated to obtain a crude product. This crude product was purified via silica gel column chromatography (n-hexane:ethyl acetate=10:1 to 5:1), and distilled under reduced pressure to obtain 823 mg of trans-whisky lactone (yield: 76.2%). This product exhibited the same physical properties as that of the trans-whisky lactone obtained in Example 1.

EXAMPLE 3

Preparation of Trans-Cognac Lactone

According to the same method as that of step [D] in example 1 with the exception that n-butyl lithium was utilized in place of n-propyl lithium, 788 mg of (3S, 4R)-3methyl-4-nonanolide (yield: 66.8%) were obtained from 1.97 g (6.93 mmol) of the tosylate obtained in step [C] of Example 1. This product exhibited the following physical properties:
m.p.: 101°-103° C./6 mmHg
$n_D^{23}$ 1.4431.
$[\alpha]_D^{23}$ +79.5° (c=0.79; CH$_2$Cl$_2$).
$^1$H NMR (CDCl$_3$): δ
0.90 (3H, t, J=6.8Hz),
1.14 (3H, d, J=6.3Hz),
1.26–1.75 (8H, m),
2.12–2.30 (2H, m),
2.60–2.75 (1H, m),
4.01 (1H, dt, J=4.0 and 7.7Hz)

EXAMPLE 4

Preparation of Eldanolide 500 mg (3.47 mmol) of the epoxide obtained in Example 2 [C'] were dissolved in 10 ml of anhydrous tetrahydrofuran. To the resultant solution, 49.8 mg (0.35 mmol) of copper bromide were further added. To the obtained mixture, Grignard reagent which had been prepared by utilizing 2-methyl propenyl bromide (2.34 g, 17.4 mmol) and magnesium (842 mg, 34.7 mmol) was slowly added dropwise under an argon atmosphere with cooling at −20° C. When the disappearance of the epoxide was confirmed by a gas chromatography, dropwise addition of the Grignard reagent was terminated. The reacted solution was poured into a saturated aqueous ammonium chloride solution, followed by extraction with diethyl ether. The obtained extract was washed with water and saturated sodium chloride aqueous solution, in this order, and dried with anhydrous sulfate. The extract was then filtered, and the filtrate was concentrated. The obtained residue wa dissolved in 10 m of methanol. The resultant solution was added to 10 ml of 10% aqueous sodium hydroxide solution, followed by stirring at room temperature for three hours. Next, methanol in the solution was distilled off under reduced pressure, and the obtained residue was extracted twice with diethyl ether and then the organic layer was separated from the obtained extract. Also, the obtained aqueous layer was acidified with dilute hydrochloric acid, and extracted five times with diethyl ether. The obtained extract was combined with the organic layer obtained before. The combined organic layer was dried with anhydrous magnesium sulfate, and concentrated to obtain a crude product. This crude product was purified via silica gel column chromatography (n-hexane:ethyl acetate=10:1 to 5:1), and distilled under reduced pressure to obtain 430 mg of (3S,4R)-3,7-dimethyl-6-octen-4-olide (eldanolide) (yield: 73.8%). This product exhibited the following physical properties:

m.p.: 115°–117° C./21 mmHg.
$n_D^{23}$ 1.4604.
$[\alpha]_D^{23}$ +52.4° (c=0.86, MeOH).
$^1$HNMR (CDCL$_3$): δ
1.14 (3H, d, J=6.5Hz),
1.64 (3H, s),
1.3 (3H, s),
2.10–2.50 (4H, m),
2.68 (1H, dd, 7.5 and 16.1Hz),
4.06 (1H, dd, J=6.5 and 12.2Hz),
5.10–5.22 (1H, m).

Additional advantages and modifications will readily occur to those skilled in the art. Therefore, the invention in its broader aspects is not limited to the specific details and illustrated examples shown and described herein. Accordingly, various modifications may be made without departing from the spirit or scope of the general inventive concept as defined by the appended claims and their equivalents.

What is claimed is:

1. A method for preparing trans-3,4-disubstituted-γ-lactones (I) of the following formula (I):

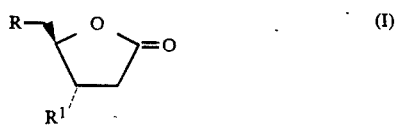

wherein R and R$^1$ are alkyl or alkenyl groups, comprising the steps of:
   (a) adding group R$^1$ to an enone group in levoglucosenone (VI) of the following general formula (VI), thereby obtaining a compound (V) of the following general formula (V),

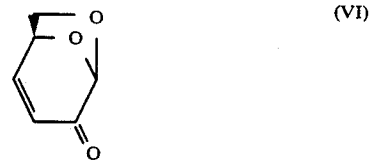

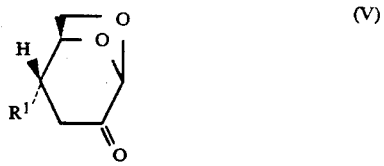

wherein R$^1$ is as indicated above;
   (b) oxidizing the obtained compound (V) with a peracid, thereby obtaining a compound (IV) of the following general formula (IV):

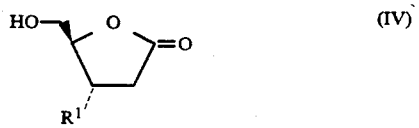

wherein R$^1$ is as indicated above;

(c) converting the hydroxyl group of the obtained compound (IV) into leaving group OR$^2$, thereby obtaining a compound (III) of the following general formula (III),

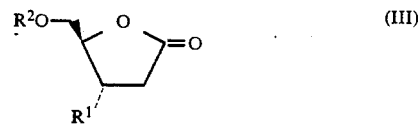

wherein R$^1$ is as indicated above, and OR$^2$ is a leaving group; and
   (d) alkylating or alkenylating the obtained compound (III) to obtain said compound (I).

2. The method according to claim 1, wherein introduction of R$^1$ to an enone group of levoglucosenone (VI) in step (a) is performed in the presence of a copper salt by utilizing an alkylating agent or an alkenylating agent.

3. The method according to claim 1, wherein R$^1$ is an alkyl group or alkenyl group which has not more than 10 carbons.

4. The method according to claim 1, wherein said peracid is selected from the group consisting of peracetic acid, performic acid, methachloro perbenzoic acid, and a peroxide of phthalic acid.

5. The method according to claim 1, wherein the conversion of the hydroxyl group to the leaving group OR$^2$ in step (c) is performed by esterification.

6. The method according to claim 1, wherein said alkylation or alkenylation in step (d) is performed in the presence of a copper salt by utilizing an alkylating agent or an alkenylating agent.

7. A method for preparing trans-3,4-disubstituted-γ-lactones (I) of the following formula (I):

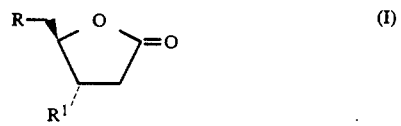

wherein R and R$^1$ are alkyl or alkenyl groups, comprising the steps of:
   (a) adding group R$^1$ to an enone group in levoglucosenone (VI) of the following general formula (VI), thereby obtaining a compound (V) of the following general formula (V),

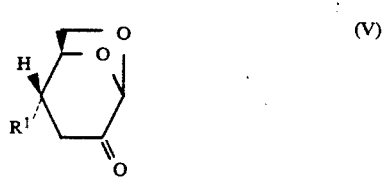

wherein R$^1$ is as indicated above;

(b) oxidizing the obtained compound (V) with a peracid, thereby obtaining a compound (IV) of the following general formula (IV):

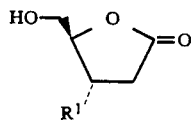

wherein $R^1$ is as indicated above;

(c) converting the hydroxyl group of the obtained compound (IV) into leaving group $OR^2$, thereby obtaining a compound (III) of the following general formula (III),

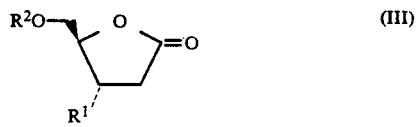

wherein $R^1$ is as indicated above, and $OR^2$ is a leaving group;

(d) treating the obtained compound (III) with a base, thereby obtaining a compound (II) of the following general formula (II):

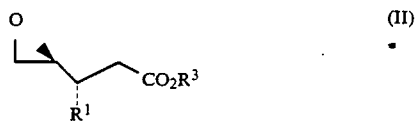

wherein $R^1$ is as indicated above, and $R^3$ is a hydrogen atom or a alkyl group; and (e) alkylating or alkenylating the obtained compound (II), thereby obtaining said compound (I).

8. The method according to claim 7, wherein introduction of $R^1$ to an enone group of levoglucosenone (VI) in step (a) is performed in the presence of a copper salt by utilizing an alkylating agent or an alkenylating agent.

9. The method according to claim 7, wherein $R^1$ is an alkyl group or alkenyl group which has not more than 10 carbons.

10. The method according to claim 7, wherein said peracid is selected from the group consisting of peracetic acid, performic acid, methachloro perbenzoic acid, and a peroxide or phthalic acid.

11. The method according to claim 7, wherein the conversion of the hydroxyl group to the leaving group $OR^2$ in step (c) is performed by esterification.

12. The method according to claim 7, wherein said alkylation or alkenylation in step (d) is performed in the presence of a copper salt by utilizing an alkylating agent or an alkenylating agent.

13. The method according to claim 7, wherein in step (d), the compound (III) is treated with a base.

14. The method according to claim 7, wherein said base is selected from the group consisting of potassium hydroxide, sodium hydroxide, lithium hydroxide, potassium carbonate, sodium carbonate, potassium acetate, and sodium acetate.

15. The method of claim 2, wherein said copper salt is selected from the group consisting of copper iodide, copper bromide, and copper chloride; said alkylating agent is selected from the group consisting of alkyl lithium and alkyl magnesium; and said alkenylating agent is selected from the group consisting of lithium and alkenyl magnesium.

16. The method of claim 2, wherein the amount of said alkylating agent or said alkenylating agent is in the range of 1.0 to 3.0 moles per one mole of said levoglucosenone.

17. The method of claim 16, wherein the amount of said alkylating agent or said alkenylating agent is 1.0 mole per one mole of said levoglucosenone.

18. The method of claim 2, the reaction is performed in an insert gas atmosphere at $-70°$ C. to room temperature, for 30 minutes to two hours, with stirring.

19. The method of claim 2, wherein the solvent is an organic solvent.

20. The method of claim 19, wherein said organic solvent is an ether, tetrahydrofuran, toluene, or xylene.

21. The method of claim 20, wherein said ether is diethyl ether.

22. The method of claim 1, wherein the amount of said peracid in step (b) is in the range of one to five moles per one mole of compound (V).

23. The method of claim 22, wherein the amount of said peracid is one mole per one mole of said compound (V).

24. The method of claim 1, wherein formation of the lactone ring in step (b) is carried out at $0°$ to $5°$ C., for one to 80 hours, with stirring, in a solvent selected from the group consisting of an acid and a halogenated solvent.

25. The method of claim 24, wherein said acid is selected from the group consisting of acetic acid and formic acid, and said halogenated solvent is selected from the group consisting of methylene chloride and chloroform.

26. The method of claim 1, wherein $R^2$ of said leaving group $OR^2$ of step (c) is selected from the group consisting of a paratoluene sulfonyl group, a methane sulfonyl group, and a trifluoromethane sulfonyl group.

27. The method of claim 1, wherein said converting of step (c) is carried out by reacting a halide of $R^2$ or an acid anhydride of $R^2$ with compound (IV) at $-10°$ to $30°$, for three to 30 hours, with stirring.

28. The method of claim 27, wherein the amount of said halide of $R^2$ or said acid anhydride of $R^2$ is in the range of one to four moles per one mole of said compound (IV).

29. The method of claim 28, wherein the amount of said halide of $R^2$ or said acid anhydride of $R^2$ is 1.3 moles per one mole of said compound (IV).

30. The method of claim 1, wherein said converting of step (c) is carried out in pyridine or triethylamine.

31. The method of claim 6, wherein said alkylating agent is selected from the group consisting of alkyl lithium and alkyl magnesium; said alkenylating agent is selected from the group consisting of alkenyl lithium and alkenyl magnesium; and said copper salt is selected from the group consisting of copper iodide, copper bromide, and copper chloride.

32. The method of claim 1, wherein said alkylating or said alkenylating of step (d) is carried out in an inert gas atmosphere, at $-70°$ to room temperature, for one to twenty hours, with stirring.

33. The method of claim 1, wherein said alkylating or said alkenylating of step (d) is carried out in an organic solvent.

34. The method of claim 33, wherein said organic solvent is toluene or xylene.

35. The method of claim 7, wherein said treating of step (d) is carried out at 0° to 30° C., for two to thirty hours, with stirring.

36. The method of claim 7, wherein said base of step (d) is selected from the group consisting of a metallic hydroxide, a carbonate, and an acetate.

37. The method of claim 36, wherein said metallic hydroxide is selected from the group consisting of potassium hydroxide, sodium hydroxide, and lithium hydroxide; said carbonate is selected from the group consisting of potassium carbonate and sodium carbonate; and said acetate is selected from the group consisting of potassium acetate and sodium acetate.

38. The method of claim 7, wherein the amount of said base in step (d) is in the range of one to three moles per one mole of compound (III).

39. The method of claim 38, wherein the amount of said base in step (d) is 1.1 moles per mole of compound (III).

40. The method of claim 7, wherein said treating of step (d) is carried out in a solvent selected from the group consisting of at least one member selected from water and an alcohol, in combination with tetrahydrofuran.

41. The method of claim 40, wherein said alcohol is methanol or ethanol.

* * * * *